United States Patent
Morita et al.

(10) Patent No.: US 7,186,023 B2
(45) Date of Patent: Mar. 6, 2007

(54) SLICE IMAGE AND/OR DIMENSIONAL IMAGE CREATING METHOD

(75) Inventors: Hisanori Morita, Kyoto-fu (JP); Shiro Oikawa, Shiga-ken (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 10/862,458

(22) Filed: Jun. 8, 2004

(65) Prior Publication Data

US 2004/0252811 A1   Dec. 16, 2004

(30) Foreign Application Priority Data

Jun. 10, 2003   (JP) .............................. 2003-165283

(51) Int. Cl.
*G01D 18/00*   (2006.01)
(52) U.S. Cl. ............................ 378/207; 378/62; 378/18
(58) Field of Classification Search .................... 378/4, 378/18, 19, 20, 62, 163, 204, 207
See application file for complete search history.

(56) References Cited

U.S. PATENT DOCUMENTS 6,493,574 B1   12/2002   Ehnholm et al. ........... 600/429
6,715,918 B2 *   4/2004   Mitschke et al. ........... 378/207

2002/0191736 A1   12/2002   Shiota ........................... 378/4

FOREIGN PATENT DOCUMENTS

JP   2003-061944   3/2003

OTHER PUBLICATIONS

Korean Office Action dated Jan. 31, 2006 (Application No. 10-2004-0042101).

* cited by examiner

*Primary Examiner*—Courtney Thomas
(74) *Attorney, Agent, or Firm*—Rader, Fishman & Grauer PLLC (57) ABSTRACT

Projection images of a calibration phantom are picked up and stored. Three-dimensional position information on an X-ray tube and an area detector is obtained from the projection images and three-dimensional arrangement information on markers inside the calibration phantom. Three-dimensional position information is obtained for all projection images, and stored in a three-dimensional position information storage unit. Projection images of an object under examination are picked up by following the same tracks and the same sequence as when radiographing the calibration phantom. Radiographic data of the projection images is read. A reconstructing calculation is carried out for the object based on the three-dimensional position information on the X-ray tube and area detector relative to the calibration phantom, to create slice images or three-dimensional volume data of a selected site of the object.

12 Claims, 9 Drawing Sheets

Fig.5 F space filter method

SLICE IMAGE AND/OR DIMENSIONAL IMAGE CREATING METHOD

BACKGROUND OF THE INVENTION (1) Field of the Invention

This invention relates to a radiographic apparatus such as a fluoroscopic table, C-arm apparatus, X-ray CT apparatus, general photographic apparatus or the like for use in the medical or industrial field. The apparatus includes an irradiating device for emitting a penetrating electromagnetic wave in a diverging form to a patient or object under examination, a planar detecting device opposed to the irradiating device across the patient or object and having a plurality of pixels arranged in an array for detecting the electromagnetic wave transmitted through the patient or object, a moving device for moving the irradiating device and planar detecting device as synchronized with each other, and an image creating device for acquiring projection images of the patient or object irradiated by the electromagnetic wave emitted from varied directions by the action of the moving device, and performing a reconstructing calculation of the projection images of the patient or object, to create slice images and/or three-dimensional images of a selected site.

(2) Description of the Related Art

This type of radiographic apparatus requires a maintenance or calibration to be carried out, for example, when collecting images of a patient or object under examination, in time of periodical inspection or in time of inspection following a trouble. The following construction is known to meet such a requirement.

According to a conventional radiographic apparatus, a calibration phantom is placed on a top board for supporting a patient or object to be examined, and a scanning device causes the irradiating device and planar or area detector to make one scanning revolution, and a projection line of a rotation sectional axis is derived from projection images thereby obtained. To prevent generation of artifacts in slice images, the irradiating device and planar detector are required to lie on a precise circular track about the rotation sectional axis. The irradiating device and planar detector are adjusted to bring a predetermined row of pixels of the planar detector into agreement with the projection line of the rotational sectional axis (see Japanese Unexamined Patent Publication 2003-61944, for example).

With the conventional apparatus, however, a rigid calibration is impossible when the track of the irradiating device and planar detector is even slightly displaced from a precise circular track about the rotation sectional axis. Further, in order to determine the projection line of the rotation sectional axis, the irradiating device and planar detector must be revolved at least 180 degrees. With a small scan range of 40 degrees, for example, a wide range scan must be performed, resulting in a drawback of requiring time and effort for a calibration.

Further, an adjustment by movement of the planar detector must also be carried out finally. A great trouble must be taken until required images are secured.

SUMMARY OF THE INVENTION

This invention has been made having the state of the art noted above, and its object is to realize a rigid calibration for preventing generation of artifacts, and to facilitate a processing for calibration for securing required images efficiently.

The above object is fulfilled, according to this invention, by a radiographic apparatus for creating slice images and/or three dimensional images from projection images obtained by detecting an electromagnetic wave emitted to an object under examination, the apparatus comprising:

an irradiating device for emitting the electromagnetic wave in a diverging form to the object;

a planar detecting device opposed to the irradiating device across the object and having a plurality of pixels in an array arrangement for detecting the electromagnetic wave transmitted through the object;

a moving device for moving the irradiating device and the planar detecting device as synchronized with each other; and an image creating device for obtaining projection images of the object by emitting the electromagnetic wave from different directions to the object by action of the moving device, and carrying out a reconstruction calculation of the projection images to create slice images and/or three-dimensional images of a selected site of the object;

wherein the image creating device obtains projection images of a calibration phantom serving as the object under examination and having at least four markers arranged three-dimensional in different planes, obtains three-dimensional position information on the irradiating device and the planar detecting device relative to the calibration phantom based on the projection images of the calibration phantom and three-dimension arrangement information on the markers inside the calibration phantom, and carries out the reconstruction calculation of the object based on the three-dimensional position information on the irradiating device and the planar detecting device.

According to this invention, three-dimensional position information on the irradiating device and the planar detecting device relative to the calibration phantom is obtained from the known three-dimension arrangement information on the markers inside the calibration phantom. It is thus possible to determine accurately from what directions and positions and how the images are projected with respect to the calibration phantom. When the calibration phantom is replaced with a patient or object to be examined, images may be picked up with the same conditions. A reconstructing calculation may be carried out for the patient or object based on the three-dimensional position information.

Thus, three-dimensional position information on the irradiating device and the planar detecting device relative to the calibration phantom may be obtained for each of the projection images. A rigid calibration may be carried out even when the irradiating device and planar detecting device make a scanning movement on tracks other than a strictly circular track. For calibration purposes, the calibration phantom may be scanned from the same range as for scanning the patient or object to be examined. Thus, the processing for calibration requires less trouble and effort than in the prior art which always requires a wide scan rage to determine a projection line of a rotation sectional axis.

The invention dispenses with a mechanical adjustment for moving the planar detector to bring a predetermined row of pixels of the planar detector into agreement with the projection line. Thus, as a whole, the processing for calibration requires a reduced time and effort to obtain required images efficiently.

In the invention described above, it is preferred that the calibration phantom includes a support member formed of a low X-ray absorber, and spherical markers formed of a high X-ray absorber. With this construction, X rays are absorbed by the spherical markers which form uniform projection images from any positions, while X rays are hardly absorbed by the support member supporting the markers. Consequently, the resulting projection images have distinct differences in shading to enable the marks to be perceived clearly, thereby accurately obtaining three-dimensional position information to obtain high-quality images.

The above markers, preferably, are steel balls.

It is preferred that the calibration phantom includes at least four markers, including a marker acting as origin of coordinates, arranged in different planes. With this construction, when images are picked up by scanning movement along precession tracks, no overlapping occurs among the markers, and the positions of the markers are easily detectable to acquire three-dimensional position information accurately. Thus, high-quality images may be obtained from a scan along precession tracks.

Preferably, the calibration phantom includes at least one marker disposed on each of an origin of XYZ coordinates, X-axis, Y-axis and Z-axis. This realizes a simple arrangement of the markers of the calibration phantom and avoids a reduction in accuracy.

It is also preferred that the calibration phantom includes at least three sets of markers, each set including two markers arranged in positions of point symmetry about an origin of coordinates, all the markers being arranged in different planes. With this construction, when images are picked up by scanning movement along circular or arcuate tracks, no overlapping occurs among the markers, and the positions of the markers are easily detectable to acquire three-dimensional position information accurately. Thus, high-quality images may be obtained from a scan along circular or arcuate tracks.

Preferably, the calibration phantom includes the markers held by a cylindrical support member. This realizes a simple and inexpensive construction of the calibration phantom and avoids a reduction in accuracy.

A preferred example of the image creating device according to the invention includes a three-dimensional position information detecting unit for obtaining the three-dimensional position information on the irradiating device and the planar detecting device relative to the calibration phantom, a three-dimensional position information storage unit for storing the three-dimensional position information obtained, and a reconstruction calculating unit for carrying out the reconstruction calculation of the object based on the three-dimensional position information stored in the three-dimensional position information storage unit, to create slice images and/or three-dimensional images of the selected site of the object.

A preferred example of the three-dimensional position information detecting unit is arranged to obtain the three-dimensional position information on the irradiating device and the planar detecting device by solving a plurality of equations formed by substituting the three-dimension arrangement information on the markers and two-dimensional position information on the projection images of the markers obtained from the projection images of the construction phantom, into a relational expression concerning a relationship between positions of the markers, the projection images of the markers, the irradiating device and the planar detecting device.

A preferred example of the reconstruction calculating unit is arranged to generate the three-dimensional volume data by back-projecting the projection images of the object to a three-dimensional lattice virtually set to a region of interest of the object.

A further preferred example of the image creating device has a slice image and three-dimensional volume data storage unit for storing the slice images and/or three-dimensional images created. Then, the images stored in the slice image and three-dimensional volume data storage unit may be read upon request.

The moving device, preferably, is arranged to rotate the irradiating device and the planar detecting device along precession tracks or arcuate tracks.

The apparatus according to this invention may further comprise an image display device for displaying the slice images and/or three-dimensional images created by the image creating device. Then, the images created by the image creating device may be displayed as appropriate.

Preferably, the irradiating device is arranged to emit X rays, and the planar detecting device is arranged to detect the X rays.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A preferred embodiment of this invention will be described in detail hereinafter with reference to the drawings.

Figure 1:
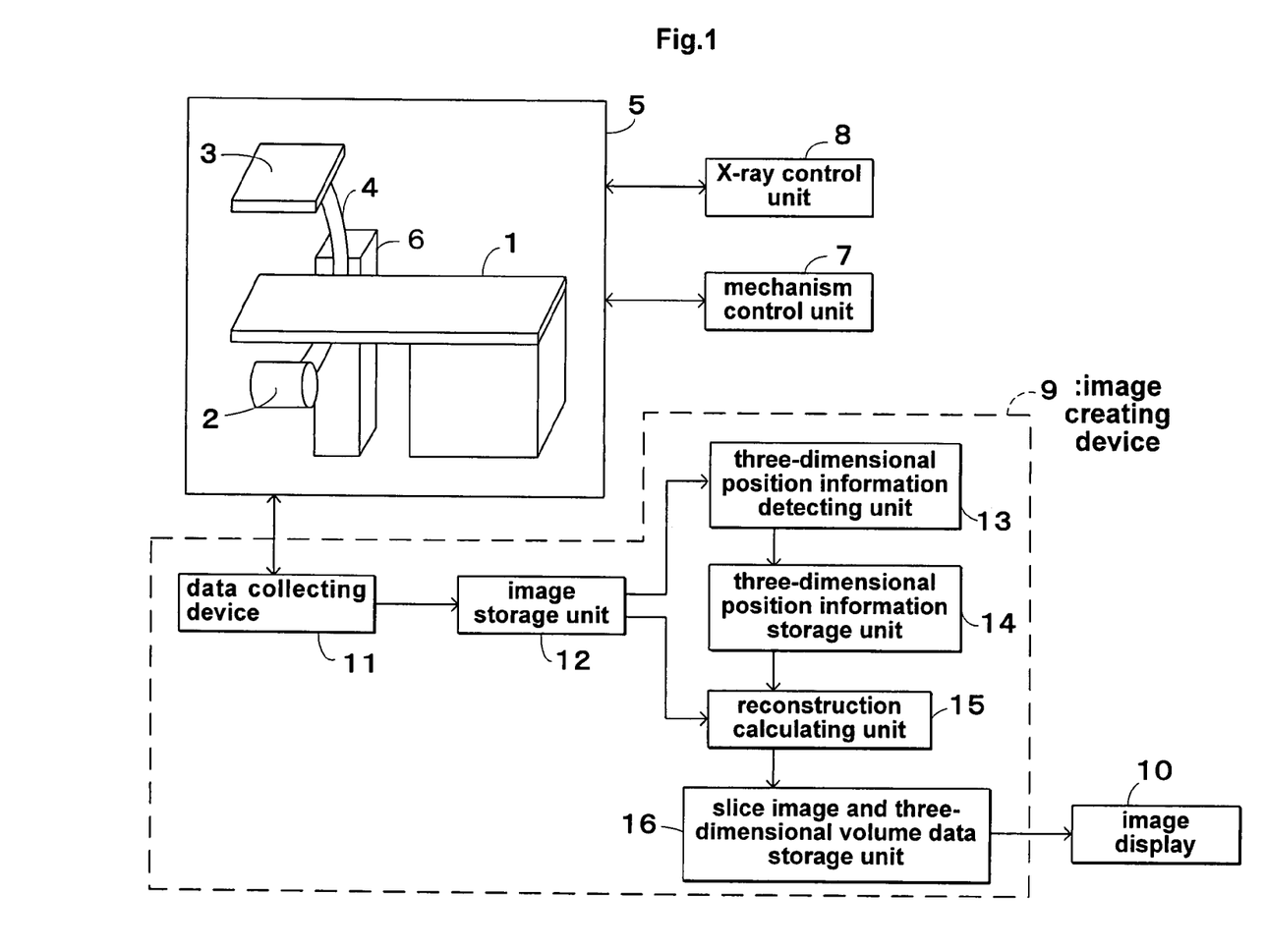
FIG. 1 is a block diagram showing a radiographic apparatus according to this invention.

FIG. 1 is a block diagram showing a radiographic apparatus according to this invention. The apparatus includes a top board 1 for supporting a patient or object under examination, and an X-ray tube 2 and an area detector 3 held by a C-shaped arm 4 to be opposed to each other across the top board 1. The X-ray tube 2 acts as an irradiating device for emitting X rays in a diverging form to the patient. The area detector 3 acts as a planar detecting device having a plurality of pixels arranged in an array for detecting X rays transmitted through the patient. These components constitute an image pickup unit 5 of the apparatus.

The C-shaped arm 4 is connected to an actuator 6 acting as a moving device to be rotatable about a horizontal axis extending longitudinally of the top board 1 and about a horizontal axis extending perpendicular to the first-mentioned horizontal axis. A mechanism control unit 7 is connected to the actuator 6 (image pickup unit 5) for rotating the C-shaped arm 4 along a precession track, circular track or arcuate track according to an object to be imaged. The actuator 6 moves the C-shaped arm 4 to move the X-ray tube 2 and area detector 3 together.

An X-ray control unit 8 is connected to the image pickup unit 5 for controlling X-ray emission from the X-ray tube 2.

An image creating device 9 is connected to the image pickup unit 5 for creating slice images and/or three-dimensional images of selected positions. An image display 10 is connected to the image creating device 9. The image display 10 corresponds to the image display device in this invention.

The image creating device 9 includes a data collecting device 11, an image storage unit 12, a three-dimensional position information detecting unit 13, a three-dimensional position information storage unit 14, a reconstruction calculating unit 15 and a slice image and three-dimensional volume data storage unit 16.

The data collecting device 11 collects data of projection images obtained by the area detector 3 of a calibration phantom [i.e. a calibration phantom FS for precession tracks or a calibration phantom FA for arcuate tracks (circular tracks) to be described hereinafter], and data of projection images obtained by the area detector 3 of the patient or object to be examined.

The image storage unit 12 stores the data of the projection images of the calibration phantom and patient collected by the data collecting device 11.

The three-dimensional position information detecting unit 13 obtains two-dimensional position information on markers (described hereinafter) of the calibration phantom from the data of the projection images of the calibration phantom stored in the image storage unit 12, and obtains three-dimensional position information on the X-ray tube 2 and area detector 3 relative to the calibration phantom from three-dimensional arrangement information on the markers in the internal structure of the calibration phantom.

The three-dimensional position information storage unit 14 stores the three-dimensional position information on the X-ray tube 2 and area detector 3 relative to the calibration phantom obtained by the three-dimensional position information detecting unit 13.

The reconstruction calculating unit 15 reads the data of the projection images of the patient picked up after the calibration phantom and stored in the image storage unit 12, performs a reconstructing calculation for the patient based on the three-dimensional position information on the X-ray tube 2 and area detector 3 relative to the calibration phantom stored in the three-dimensional position information storage unit 14, and creates slice image and/or three-dimensional volume data of a selected site of the patient.

The slice image and three-dimensional volume data storage unit 16 stores the slice image and/or three-dimensional volume data of the selected site of the patient created from the reconstructing calculation performed by the reconstruction calculating unit 15, and outputs the data to the image display 10 as necessary.

Figure 2:
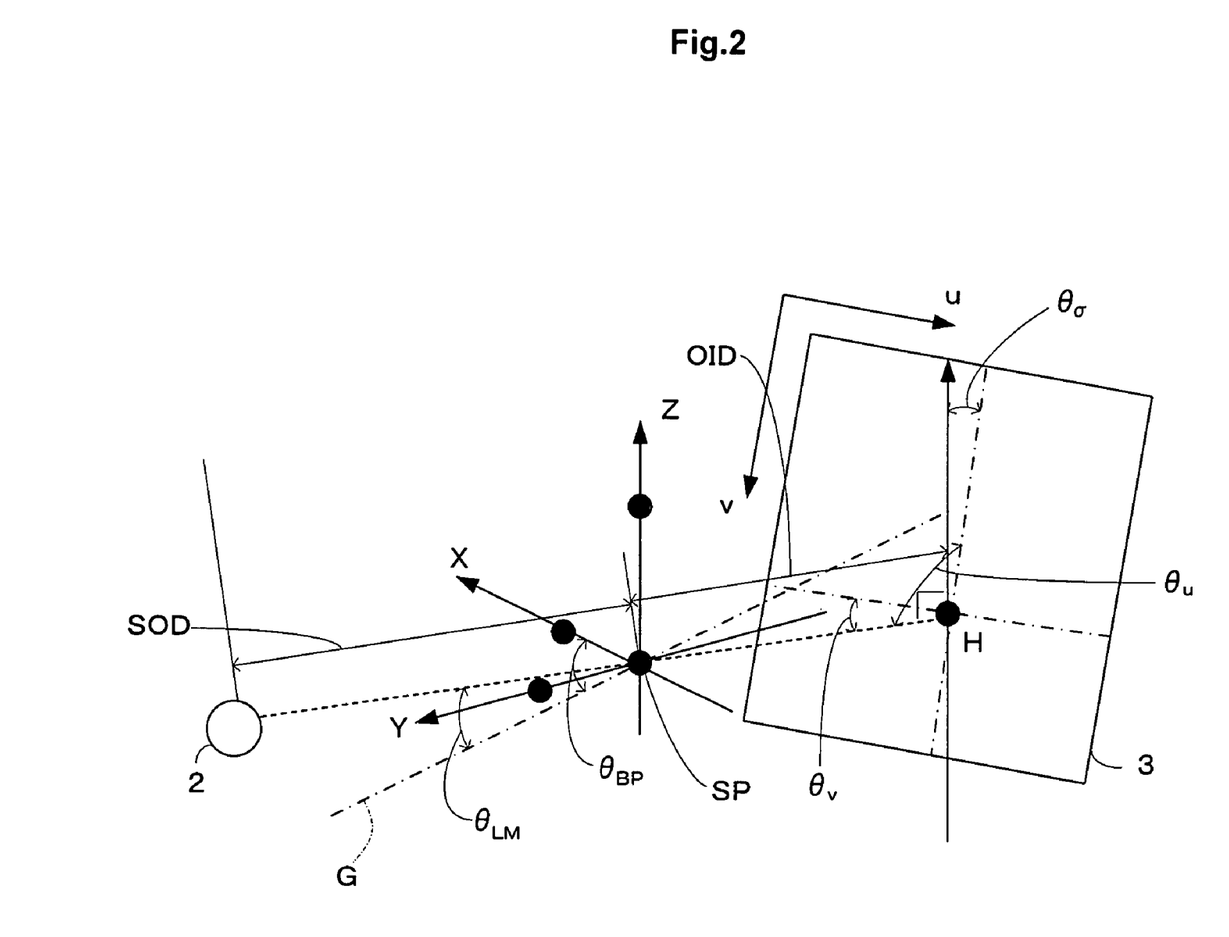
FIG. 2 is an explanatory view of three-dimensional position information.

The above-noted three-dimensional position information comprises nine degrees of freedom which are, as shown in the explanatory view in FIG. 2, three degrees of freedom (positions) with the X-ray tube 2 regarded as one point, and six degrees of freedom (positions and inclining directions) of the area detector 3. The particulars are set out below. The alternate long and short dash line G represents a projection line to an X-Y plane of an axis linking the X-ray tube 2 and a starting point SP.

SOD: distance from the starting point (i.e. the starting point of the calibration phantom) SP to the X-ray tube 2;

BP angle: azimuth angle of X-ray tube 2;

LM angle: elevation angle of X-ray tube 2;

OID: distance from the starting point SP to the area detector 3 along X rays passing through the starting point SP;

CENTER: u coordinates of point H at which X rays passing through the starting point SP impinge on the area detector 3;

MIDDLE: v coordinates of point H at which X rays passing through the starting point SP impinge on the area detector 3;

σ angle: angle between the direction along v-axis of the area detector 3 and a projection image along Z-axis of the calibration phantom (σ angle=θσ);

u inclination: inclination angle about X rays passing through the starting point SP and u-axis of the area detector 3 (u inclination=θu−90°);

v inclination: inclination angle about X rays passing through the starting point SP and v-axis of the area detector 3 (v inclination=θv−90°).

Figure 3:
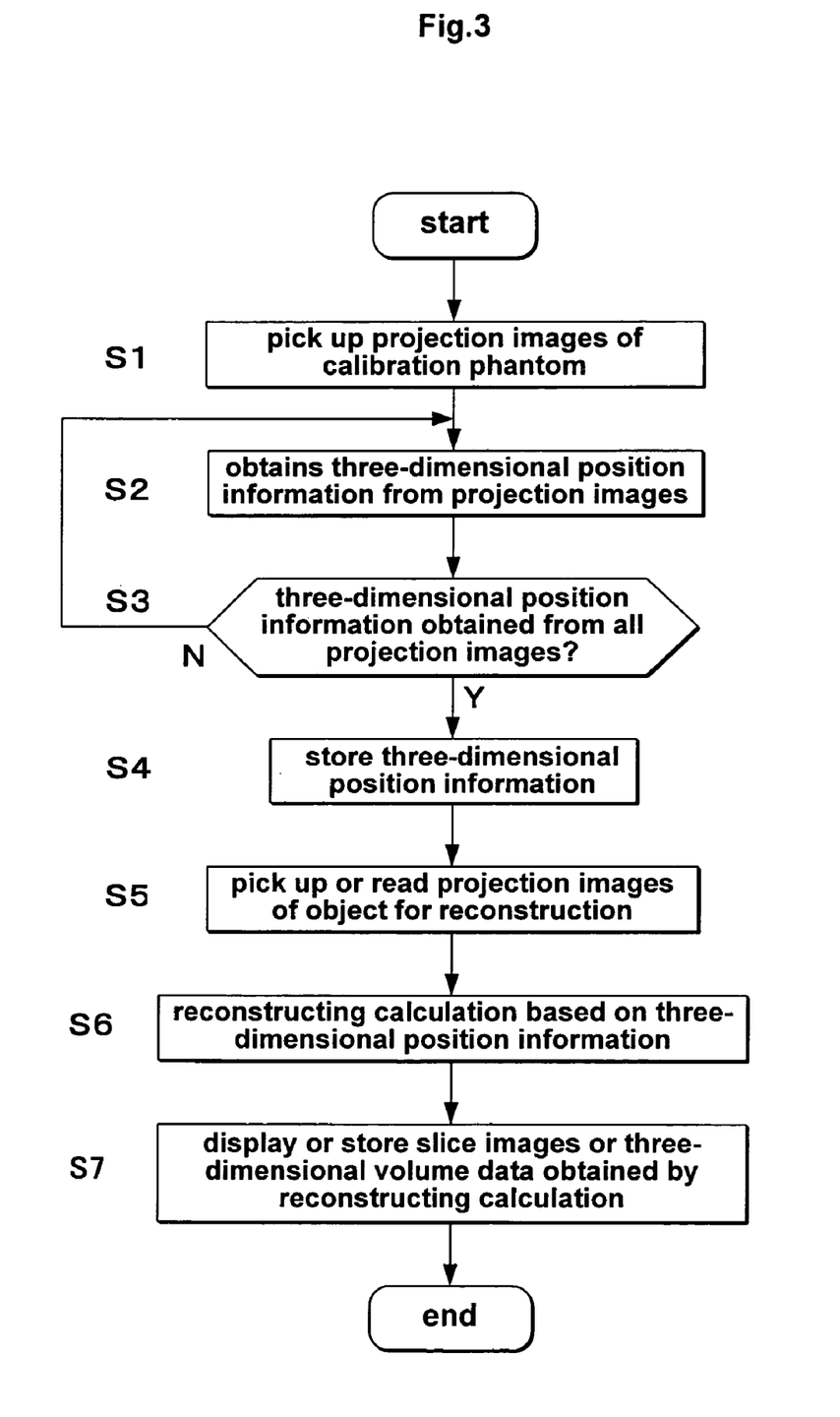
FIG. 3 is a flow chart showing an image creating operation of the radiographic apparatus according to this invention.

Next, a processing operation by the image creating device 9 will be described with reference to the flow chart of FIG. 3.

First, while the mechanism control unit 7 rotates the C-shaped arm 4, the X-ray control unit 8 controls the X-ray tube 2 to emit X rays, to pick up projection images of the calibration phantom (S1). The data collecting device 11 collects the projection images from the area detector 3, which are stored in the image storage unit 12. The three-dimensional position information detecting unit 13 obtains three-dimensional position information on the X-ray tube 2 and area detector 3 from the projection images and three-dimensional arrangement information on the markers inside the calibration phantom (S2).

After obtaining three-dimensional position information from all the projection images (S3), the three-dimensional position information is stored in the three-dimensional position information storage unit 14 (S4).

A fixed relationship is established between positions of the X-ray tube 2, area detector 3, markers, and the projection images of the markers. These positions are all positions relative to the calibration phantom, and specifically are coordinate information on XYZ coordinates of the starting point SP shown in FIG. 2. The X-ray tube 2, markers, and the projection images of the markers are point positions, while the position of the area detector 3 is a planar position. The markers are provided inside the calibration phantom, and the coordinates of the marker are known in advance.

The above fixed relationship may be expressed by a relational expression concerning the relationship between the positions of the markers, the projection images of the markers, X-ray tube 2 and area detector 3. An equation is formed by substituting information on each marker into the relational expression. By resolving this equation for each component of the XYZ coordinates, three equations are formed for each marker. The three-dimensional position information on the X-ray tube 2 and area detector 3 to be obtained comprises the nine unknown pieces of information noted hereinbefore. Thus, the three-dimensional position information may be obtained by solving 12 simultaneous equations derived from four markers.

Figure 4:
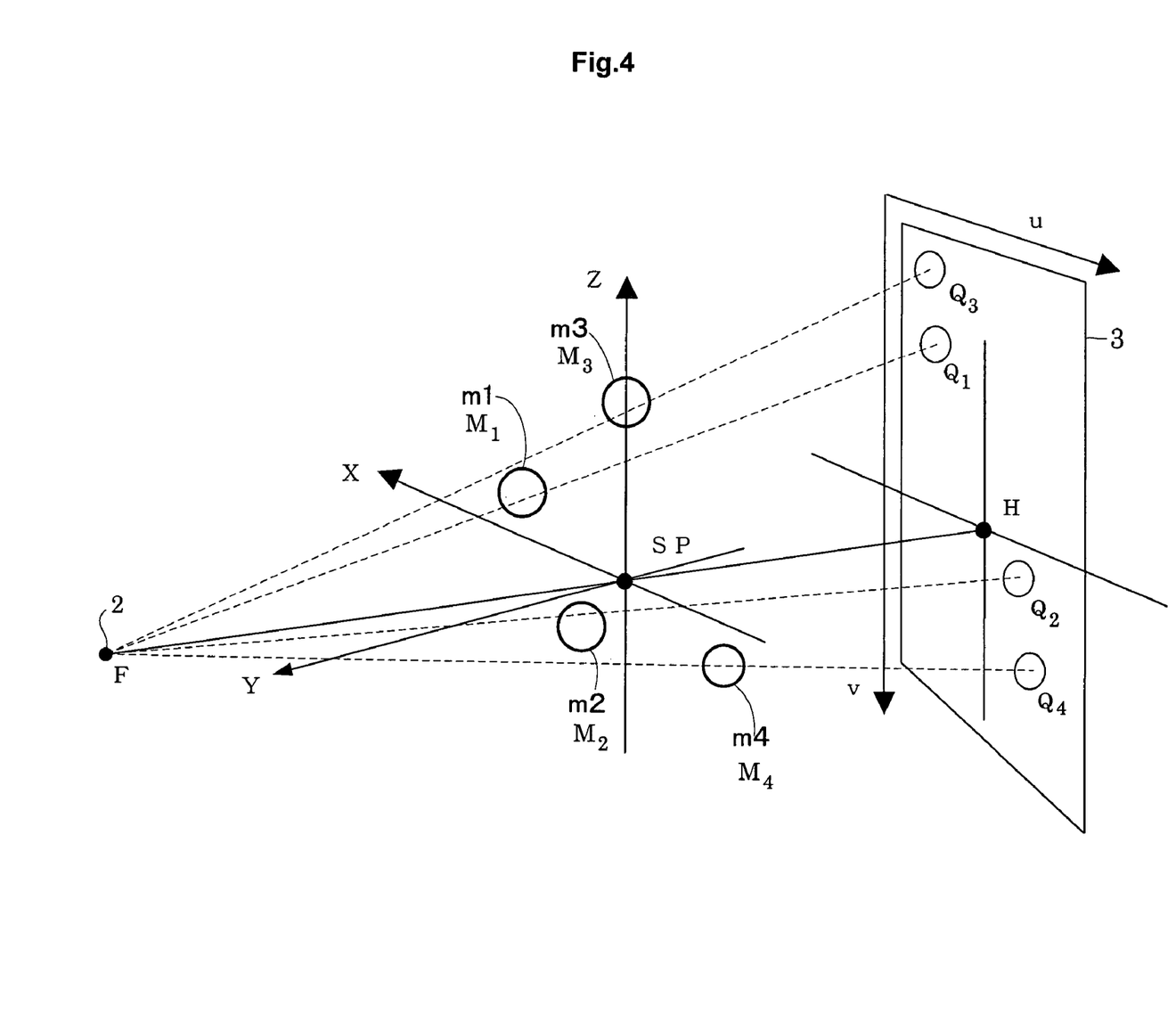
FIG. 4 is an explanatory view illustrating a determination of three-dimensional position information on an X-ray tube and an area detector.

An example thereof will be described hereinafter with reference to FIG. 4. Assume that four markers m1, m2, m3 and m4 are arranged three-dimensionally as shown in FIG. 4. In the XYZ coordinates with the starting point SP serving as the origin, point $M_1$, point $M_2$, point $M_3$ and point $M_4$ are assumed coordinates constituting three-dimensional arrangement information on the markers m1, m2, m3 and m4. The points $M_1$ to $M_4$ are known. The XYZ coordinates of X-ray tube 2 are assumed to be point F. Point F is unknown. It is further assumed that, when the X-ray tube 2 emits X rays, images of the markers m1, m2, m3 and m4 are projected to XYZ coordinate points $Q_1$, $Q_2$, $Q_3$ and $Q_4$ on the area detector 3, respectively. The XYZ coordinates of the points $Q_1$–$Q_4$ are unknown since the position information on the area detector 3 itself is unknown. However, the coordinates on the area detector 3 (uv coordinates) which constitute two-dimensional position information on the projection images of the markers m1–m4 are obtained from the projection images detected, and are therefore known.

The following group of equations (1) is formed concerning vectors $\overrightarrow{SPQ_1}$–$\overrightarrow{SPQ_4}$ from the starting point SP to the points $Q_1$–$Q_4$:

$$\overrightarrow{SPQ_1} = \overrightarrow{SPM_1} + \overrightarrow{M_1Q_1}$$

$$\overrightarrow{SPQ_2} = \overrightarrow{SPM_2} + \overrightarrow{M_2Q_2}$$

$$\overrightarrow{SPQ_3} = \overrightarrow{SPM_3} + \overrightarrow{M_3Q_3}$$

$$\overrightarrow{SPQ_4} = \overrightarrow{SPM_4} + \overrightarrow{M_4Q_4} \quad (1)$$

On the other hand, assuming a straight line extending through the point F and starting point SP reaches point H on the area detector 3, vectors $\overrightarrow{SPQ_1}$–$\overrightarrow{SPQ_4}$ from the starting point SP to the points $Q_1$–$Q_4$ may be expressed by the following group of equations (2):

$$\overrightarrow{SPQ_1} = \overrightarrow{SPH} + \overrightarrow{HQ_1}$$

$$\overrightarrow{SPQ_2} = \overrightarrow{SPH} + \overrightarrow{HQ_2}$$

$$\overrightarrow{SPQ_3} = \overrightarrow{SPH} + \overrightarrow{HQ_3}$$

$$\overrightarrow{SPQ_4} = \overrightarrow{SPH} + \overrightarrow{HQ_4} \quad (2)$$

From the group of equations (1) and the group of equations (2), the relationship between the markers, the projection images of the markers, X-ray tube 2 and area detector 3 is expressed by the following group of equations (3):

$$\overrightarrow{SPM_1} + \overrightarrow{M_1Q_1} = \overrightarrow{SPH} + \overrightarrow{HQ_1}$$

$$\overrightarrow{SPM_2} + \overrightarrow{M_2Q_2} = \overrightarrow{SPH} + \overrightarrow{HQ_2}$$

$$\overrightarrow{SPM_3} + \overrightarrow{M_3Q_3} = \overrightarrow{SPH} + \overrightarrow{HQ_3}$$

$$\overrightarrow{SPM_4} + \overrightarrow{M_4Q_4} = \overrightarrow{SPH} + \overrightarrow{HQ_4} \quad (3)$$

Each equation in the group of equations (3) has the three components, i.e. X component, Y component and Z component of the XYZ coordinates, and may be resolved into three relational expressions for the respective components. Equations are formed by substituting the XYZ coordinates of the known points $M_1$–$M_4$ and uv coordinates of the known projection images into this group of equations (3).

When each of the equations is resolved into three equations for the respective components of XYZ coordinates, 12 simultaneous equations in total are formed. By solving these 12 simultaneous equations, the three-dimensional position information on the X-ray tube 2 and area detector 3 can be obtained.

The relational expressions shown in the group of equations (3) will be described in detail. First, since the starting point SP and points $M_1$–$M_4$ are known beforehand, vector $\overrightarrow{SPM_1}$–vector $\overrightarrow{SPM_4}$ are known. For vector $\overrightarrow{M_1Q_1}$, the following group of equations (4) is formed since points $Q_1$–$Q_4$ are located on the straight lines linking point F and points $M_1$–$M_4$:

$$\overrightarrow{M_1Q_1} = (1-r_1)(\overrightarrow{SPF} - \overrightarrow{SPM_1})$$

$$\overrightarrow{M_2Q_2} = (1-r_2)(\overrightarrow{SPF} - \overrightarrow{SPM_2})$$

$$\overrightarrow{M_3Q_3} = (1-r_3)(\overrightarrow{SPF} - \overrightarrow{SPM_3})$$

$$\overrightarrow{M_4Q_4} = (1-r_4)(\overrightarrow{SPF} - \overrightarrow{SPM_4}) \quad (4)$$

Here, coefficients $r_1$–$r_4$ are unknown real numbers that satisfy the following group of equations (5):

$$\overrightarrow{FQ_1} = r_1 \times \overrightarrow{FM_1}$$

$$\overrightarrow{FQ_2} = r_2 \times \overrightarrow{FM_2}$$

$$\overrightarrow{FQ_3} = r_3 \times \overrightarrow{FM_3}$$

$$\overrightarrow{FQ_4} = r_4 \times \overrightarrow{FM_4} \quad (5)$$

Further, vector $\overrightarrow{SPF}$ is equal to a product of unit vector $\overrightarrow{U_{SPF}}$ from the starting point SP toward point F and the distance SOD from the starting point SP to point F. The vector $\overrightarrow{SPH}$ included in the right-hand side in the group of equations (3) are also equal to a product of unit vector $\overrightarrow{U_{SPH}}$ from the starting point SP toward point H and the distance OID from the starting point SP to point H. Further, a relationship $\overrightarrow{U_{SPH}} = -\overrightarrow{U_{SPF}}$ is formed. Therefore, vectors $\overrightarrow{SPF}$ and $\overrightarrow{SPH}$ may be expressed by the following group of equations (6):

$$\overrightarrow{SPF} = SOD \times \overrightarrow{U_{SPF}} = SOD \times R_{BP} R_{LM} \begin{pmatrix} 1 \\ 0 \\ 0 \end{pmatrix} \quad (6)$$

$$\overrightarrow{SPH} = OID \times \overrightarrow{U_{SPH}} = OID \times R_{BP} R_{LM} \begin{pmatrix} -1 \\ 0 \\ 0 \end{pmatrix}$$

where $R_{BP}$ and $R_{LM}$ are rotation matrices shown in the following equations (7) and (8):

$$R_{BP} = \begin{bmatrix} \cos\theta_{BP} & -\sin\theta_{BP} & 0 \\ \sin\theta_{BP} & \cos\theta_{BP} & 0 \\ 0 & 0 & 1 \end{bmatrix} \quad (7)$$

-continued $$R_{LM} = \begin{bmatrix} \cos\theta_{LM} & 0 & -\sin\theta_{LM} \\ 0 & 1 & 0 \\ \sin\theta_{LM} & 0 & \cos\theta_{LM} \end{bmatrix} \quad (8)$$

As seen from the above equations, the rotation matrix $R_{BP}$ is a rotation by BP angle ($\theta_{BP}$) about Z-axis of the straight line FH, and the rotation matrix $R_{LM}$ is a rotation by LM angle ($\theta_{LM}$) about -Y-axis of the straight line FH. SOD, OID, $\theta_{BP}$, and $\theta_{LM}$ are all unknown.

Lastly, vectors $\overrightarrow{HQ_1}$–$\overrightarrow{HQ_4}$ will be described. Assume that the coordinates (uv coordinates) on the area detector 3 of the projection images of the markers are $(s_1, t_1)$, $(s_2, t_2)$, $(s_3, t_3)$ and $(s_4, t_4)$, respectively. Assume also that the coordinates (uv coordinates) on the area detector 3 of point H are (CENTER, MIDDLE). Assume further that unit vectors along the u-axis and v-axis of the area detector 3 are $\overrightarrow{U_u}$ and $\overrightarrow{U_v}$, respectively. Then, vectors $\overrightarrow{HQ_1}$–$\overrightarrow{HQ_4}$ may be expressed by the following group of equations (9):

$$\overrightarrow{HQ_1} = (s_1 - \text{CENTER})\overrightarrow{U_u} + (t_1 - \text{MIDDLE})\overrightarrow{U_v}$$

$$\overrightarrow{HQ_2} = (s_2 - \text{CENTER})\overrightarrow{U_u} + (t_2 - \text{MIDDLE})\overrightarrow{U_v}$$

$$\overrightarrow{HQ_3} = (s_3 - \text{CENTER})\overrightarrow{U_u} + (t_3 - \text{MIDDLE})\overrightarrow{U_v}$$

$$\overrightarrow{HQ_4} = (s_4 - \text{CENTER})\overrightarrow{U_u} + (t_4 - \text{MIDDLE})\overrightarrow{U_v} \quad (9)$$

In the group of equations (9), $s_1$–$s_4$, and $t_1$–$t_4$ are known, and CENTER, MIDDLE and unit vectors $\overrightarrow{U_u}$ and $\overrightarrow{U_v}$ are unknown.

The uv plane may be considered a result of rotation of a plane parallel to YZ plane. Therefore, unit vectors are given by rotating unit vectors $\overrightarrow{U_u}$ and $\overrightarrow{U_v}$ along Y-axis and -Z-axis, respectively. Specifically, these vectors are expressed by the following group of equations (10):

$$\overrightarrow{U_u} = R_{BP}R_{LM}R_vR_uR_\sigma \begin{pmatrix} 0 \\ 1 \\ 0 \end{pmatrix} \quad (10)$$

$$\overrightarrow{U_v} = R_{BP}R_{LM}R_vR_uR_\sigma \begin{pmatrix} 0 \\ 0 \\ -1 \end{pmatrix}$$

where $R_u$ is a rotation matrix (about an axis parallel to Y-axis when $\theta_{BP}=0$ and $\theta_{LM}=0$) corresponding to the u inclination ($\theta_u$–90°) of the area detector 3, which is expressed by equation (11) below. $R_v$ is a rotation matrix (about an axis parallel to Z-axis when $\theta_{BP}=0$ and $\theta_{LM}=0$) corresponding to the v inclination ($\theta_v$–90°) of the area detector 3, which is expressed by equation (12) below. Further, $R\sigma$ is a rotation matrix (about an axis parallel to X-axis when $\theta_{BP}=0$ and $\theta_{LM}=0$) corresponding to the $\sigma$ angle ($\theta\sigma$) of the area detector 3, which is expressed by equation (13) below. $\theta_u$, $\theta_v$ and $\theta_\sigma$ are all unknown.

$$R_u = \begin{bmatrix} \cos\theta_u & 0 & -\sin\theta_u \\ 0 & 1 & 0 \\ \sin\theta_u & 0 & \cos\theta_u \end{bmatrix} \quad (11)$$

$$R_v = \begin{bmatrix} \cos\theta_v & \sin\theta_v & 0 \\ -\sin\theta_v & \cos\theta_v & 0 \\ 0 & 0 & 1 \end{bmatrix} \quad (12)$$

$$R_\sigma = \begin{bmatrix} 1 & 0 & 0 \\ 0 & \cos\theta_\sigma & \sin\theta_\sigma \\ 0 & -\sin\theta_\sigma & \cos\theta_\sigma \end{bmatrix} \quad (13)$$

Twelve specific equations are formed by substituting the information obtained about the four markers into and rearranging the group of equations (3). That is, by substituting the group of equations (4), the group of equations (6), the group of equations (9) and the group of equations (10) into the four relational expressions in the group of equations (3), the following four equations (14), (15), (16) and (17) are formed:

$$r_1\overrightarrow{SPM_1} + (1-r_1)\left(SOD \times R_{BP}R_{LM}\overrightarrow{SPM_1}\right) = \quad (14)$$

$$\left(OID \times R_{BP}R_{LM}\begin{pmatrix} -1 \\ 0 \\ 0 \end{pmatrix}\right) + (s_1 - \text{CENTER})R_{BP}R_{LM}R_vR_uR_\sigma\begin{pmatrix} 0 \\ 1 \\ 0 \end{pmatrix} +$$

$$(t_1 - \text{MIDDLE})R_{BP}R_{LM}R_vR_uR_\sigma\begin{pmatrix} 0 \\ 0 \\ -1 \end{pmatrix}$$

$$r_2\overrightarrow{SPM_2} + (1-r_2)\left(SOD \times R_{BP}R_{LM}\overrightarrow{SPM_2}\right) = \quad (15)$$

$$\left(OID \times R_{BP}R_{LM}\begin{pmatrix} -1 \\ 0 \\ 0 \end{pmatrix}\right) + (s_2 - \text{CENTER})R_{BP}R_{LM}R_vR_uR_\sigma\begin{pmatrix} 0 \\ 1 \\ 0 \end{pmatrix} +$$

$$(t_2 - \text{MIDDLE})R_{BP}R_{LM}R_vR_uR_\sigma\begin{pmatrix} 0 \\ 0 \\ -1 \end{pmatrix}$$

$$r_3\overrightarrow{SPM_3} + (1-r_3)\left(SOD \times R_{BP}R_{LM}\overrightarrow{SPM_3}\right) = \quad (16)$$

$$\left(OID \times R_{BP}R_{LM}\begin{pmatrix} -1 \\ 0 \\ 0 \end{pmatrix}\right) + (s_3 - \text{CENTER})R_{BP}R_{LM}R_vR_uR_\sigma\begin{pmatrix} 0 \\ 1 \\ 0 \end{pmatrix} +$$

$$(t_3 - \text{MIDDLE})R_{BP}R_{LM}R_vR_uR_\sigma\begin{pmatrix} 0 \\ 0 \\ -1 \end{pmatrix}$$

$$r_4\overrightarrow{SPM_4} + (1-r_4)\left(SOD \times R_{BP}R_{LM}\overrightarrow{SPM_4}\right) = \quad (17)$$

$$\left(OID \times R_{BP}R_{LM}\begin{pmatrix} -1 \\ 0 \\ 0 \end{pmatrix}\right) + (s_4 - \text{CENTER})R_{BP}R_{LM}R_vR_uR_\sigma\begin{pmatrix} 0 \\ 1 \\ 0 \end{pmatrix} +$$

$$(t_4 - \text{MIDDLE})R_{BP}R_{LM}R_vR_uR_\sigma\begin{pmatrix} 0 \\ 0 \\ -1 \end{pmatrix}$$

Since each of the equations (14), (15), (16) and (17) may be resolved into three equations for the respective components of XYZ coordinates, a total of 12 equations is obtained from the equations (14)–(17).

Here, as noted in the foregoing description, the unknowns are 13 in total which are nine (SOD, OID, CENTER, MIDDLE, $\theta_{BP}$, $\theta_{LM}$, $\theta_u$, $\theta_v$ and $\theta_o$) constituting the three-dimensional position information on the X-ray tube 2 and area detector 3, and four coefficients $r_1$–$r_4$.

Thus, the number of simultaneous equations is smaller than the number of unknowns by one. In this case, the 13 unknowns may be estimated by repeated calculation using least squares. A procedure thereof will particularly be described hereinafter.

(Process 1)

Assuming that the radiographic apparatus is free of bends and distortions, theoretical values of the above 13 unknowns are first derived from sizes of the materials of the apparatus and rotation angles instructed from the mechanism control unit 7 to the actuator 6. The theoretical values of the 13 unknowns will be called "initial values".

(Process 2)

The coordinates of points $M_1$, $M_2$, $M_3$ and $M_4$ constituting the three-dimensional arrangement information on markers m1, m2, m3 and m4 are substituted into equations (14) to (17). No substitution is made of values (hereinafter called "measured values") of $s_1$–$s_4$ and $t_1$–$t_4$ which are the coordinates (uv coordinates) of the projection images of markers m1–m4 observed on the area detector 3.

(Process 3)

The "initial values" are assigned to the 13 unknowns in equations (14) to (17) into which the three-dimensional arrangement information on the markers has been substituted. These equations are solved for eight values of $s_1$–$s_4$ and $t_1$–$t_4$. At this time, the eight values sought may be determined analytically from the 12 simultaneous equations. The values of $s_1$–$s_4$ and $t_1$–$t_4$ thereby obtained will be called "reverse operation values".

Then, differences between the "measured values" and "reverse operation values" of $s_1$–$s_4$ and $t_1$–$t_4$ are determined. The differences between the "measured values" and "reverse operation values" of $s_1$, $s_2$, $s_3$ and $s_4$ will be called $\Delta 1$, $\Delta 2$, $\Delta 3$ and $\Delta 4$, respectively. The differences between the "measured values" and "reverse operation values" of $t_1$, $t_2$, $t_3$ and $t_4$ will be called $\Delta 5$, $\Delta 6$, $\Delta 7$ and $\Delta 8$, respectively.

Further, a total of squares of the differences is derived from the following equation (18). This value will be hereinafter called "error square sum a".

$$a = \sum_{i=1}^{8} (\Delta i)^2 \quad (18)$$

(Process 4)

Next, "error square sum a" is obtained for each of the 13 unknowns by repeating the calculation shown in Process 3 on slightly varied values. Then, a case of providing the smallest "error square sum a" is identified. A step quantity for making the varied values is an empirically obtained effective value.

Specifically, where the initial value of CENTER which is one of the unknowns is "$C_0$" and the step quantity for varying this value is "$\Delta C$", a sum of the initial value and the step quantity ($C_0 + \Delta C$) is assigned to CENTER, and the initial values are assigned to the other 12 unknowns, in equations (14) to (17). Then, an "error square sum a" is determined from the equations. Next, a difference between the initial value and the step quantity ($C_0 - \Delta C$) is assigned to CENTER, and the initial values are assigned to the other 12 unknowns, in equations (14) to (17). Then, an "error square sum a" is determined from the equations. This calculation is performed successively for the 12 remaining unknowns such as MIDDLE while adding and subtracting the step quantity. Thus, Process 4 results in 26 different "error square sums a" (that is, 13 obtained by adding the step quantity to the initial values of the 13 unknowns, and 13 obtained by subtracting the step quantity from the initial values of the 13 unknowns).

The above-noted way of varying the "initial values" is shown as an example, and may be selected and changed as appropriate. While 26 "error square sums a" are obtained in the above example, this number, of course, is not limitative.

(Process 5)

The case where the value of "the error square sum a" is the smallest of all the "error square sums a" obtained from processes 3 and 4 is identified. The values assigned to the 13 unknowns at this time are replaced with the "initial values" of the 13 unknowns.

When the "initial values" are varied as described in Process 4, 27 "error square sums a" in total are obtained from Processes 3 and 4. When the smallest "error square sum a" is provided by the case of the sum of the initial value and the step quantity ($C_0 + \Delta C$) being assigned to CENTER and the "initial values" being assigned to the other 12 unknowns, only the initial value of CENTER is replaced with $C_0 + \Delta C$.

Next, the smallest "error square sum a" identified is compared with a predetermined, specified value of the "error square sum a" (hereinafter called simply "specified value") to determine whether the value of the smallest "error square sum a" is less than the specified value.

When the value of the smallest "error square sum a" is found equal to or greater than the specified value, the operation returns to Process 3 to repeat the same calculation using the replaced initial values of the 13 unknowns, to determine a new value of the smallest "error square sum a" and replace the initial values of the 13 unknowns. By repeating the calculation in this way, the value of "the error square sum a" gradually becomes smaller.

On the other hand, when the value of the smallest "error square sum a" is found less than the specified value, the initial values of the 13 unknowns are presumed to be the values of the 13 unknowns, respectively. Then, the series of calculations is ended.

What is an appropriate specified value, that is at what point of convergence of the value of "error square sum a" the calculations may end, is dependent on the resolution of the area detector 3.

For example, where the area detector 3 has a square arrangement of pixels and the differences of $s_1$–$s_4$ and $t_1$–$t_4$ are, on average, less than a half of a distance $D_D$ between the pixels corresponding to one side of the square, the resolution is considered satisfactory for the radiographic apparatus. In this case, therefore, the specified value may be set to $2D_D^2$. If this satisfies the following equation (19), the series of calculation may be ended:

$$a_{\min} < 2D_D^2 \left(\frac{1}{2} D_D\right)^2 \times 8 \quad (19)$$

where $a_{min}$ is the smallest "error square sum a" identified in Process 5.

The above-noted way of determining a specified value also is shown as an example, and may be selected and varied as appropriate.

The above is a procedure of estimating the 13 unknowns by the repeated calculation using least squares.

With an increased number of markers, the unknowns may be estimated analytically without relying on the repeated calculation using least squares. In this case, the estimation may be carried out at increased speed and with increased accuracy.

The technique of obtaining the three-dimensional position information on the X-ray tube and area detector is the same also for the case of calibration phantom FS for precession tracks or calibration phantom FA for arcuate tracks to be described hereinafter.

The processing operation by the image creating device 9 will be described further by referring to FIG. 3. Subsequently, projection images of the patient are picked up for reconstruction by following the same tracks and the same sequence as when radiographing the calibration phantom. The projection images are stored in the image storage unit 12, or radiographic data of the projection images of the patient is read from the image storage unit 12 (S5).

Slice images or three-dimensional volume data of a selected site of the patient are created by performing reconstructing calculations based on the radiographic data of the projection images of the patient and the three-dimensional position information on the X-ray tube 2 and area detector 3 relative to the calibration phantom stored in the three-dimensional position information storage unit 14 (S6).

Figure 5:
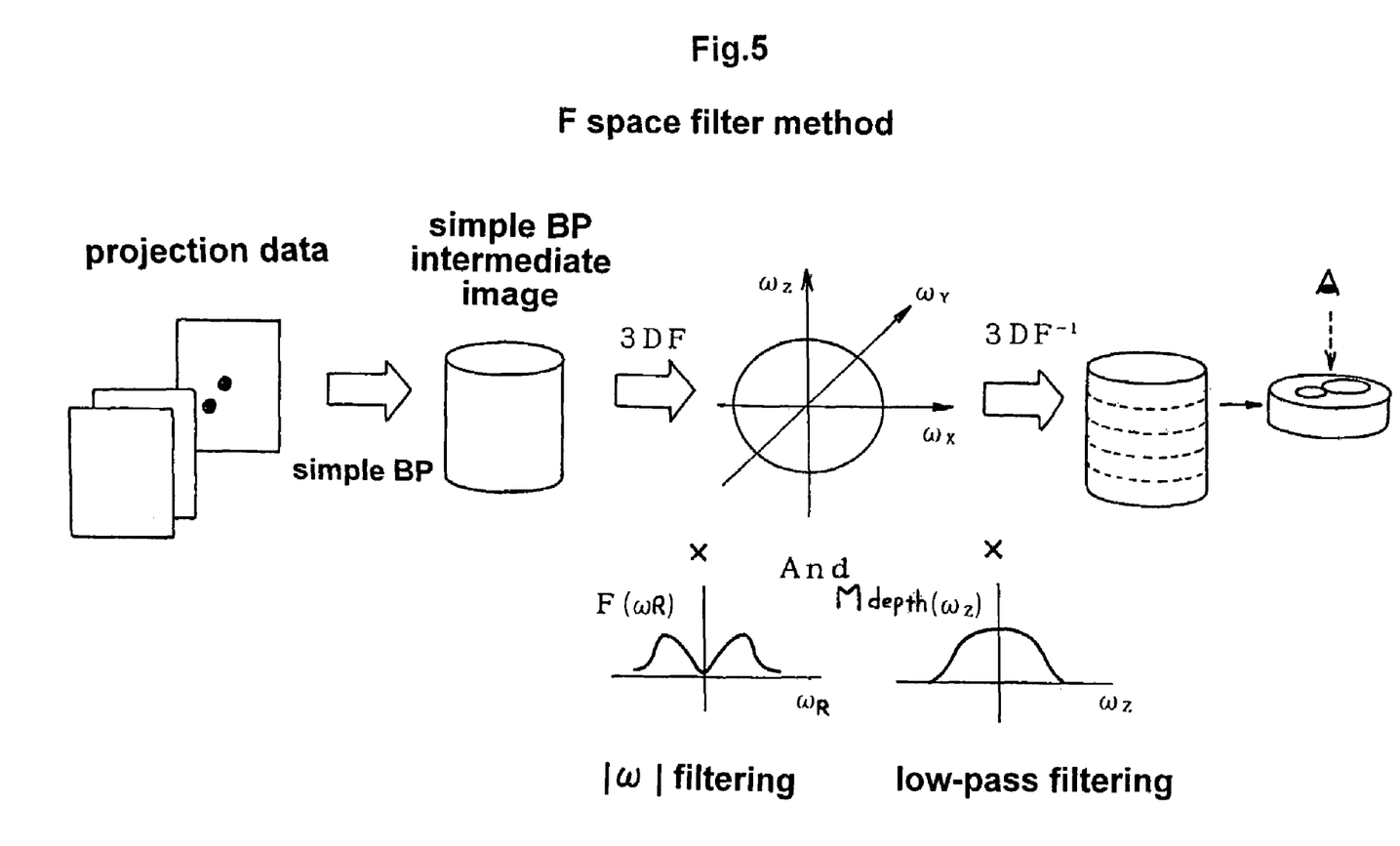
FIG. 5 is a schematic view illustrating a procedure for creating three-dimensional volume data.

A series of processing steps for creating the three-dimensional volume data will be outlined with reference to FIG. 5. First, the group of projection data is subjected to a simple back projection (simple BP) to generate a simple BP intermediate image. Next, the simple BP intermediate image is subjected to a three-dimensional Fourier transform to generate a three-dimensional Fourier distribution image which is Fourier space data converted from real space data (in FIG. 5, the three-dimensional Fourier distribution image is shown in three-dimensional Fourier space coordinates). Next, the three-dimensional Fourier distribution image receives a filtering process ($|\omega|$ filtering (absolute value omega filtering) and low-pass filtering). Next, the three-dimensional Fourier distribution image filtered is subjected to a three-dimensional back Fourier transform to change the Fourier space data back to real space data and to generate three-dimensional volume data (in FIG. 5, this corresponds to the cylindrical object shown toward the right-hand end, with several dotted lines extending circumferentially). The image reconstruction is carried out in this way to generate three-dimensional volume data of the region of interest. The operator may observe an image of any slice plane selected from the three-dimensional volume data (in FIG. 5, this corresponds to the thin cylindrical object shown at the extreme right-hand end). As noted above, a simple BP intermediate image is generated once, and a predetermined filtering process is carried out for the simple BP intermediate image in the Fourier space. This procedure is called an F (Fourier) space filter method.

Figure 6:
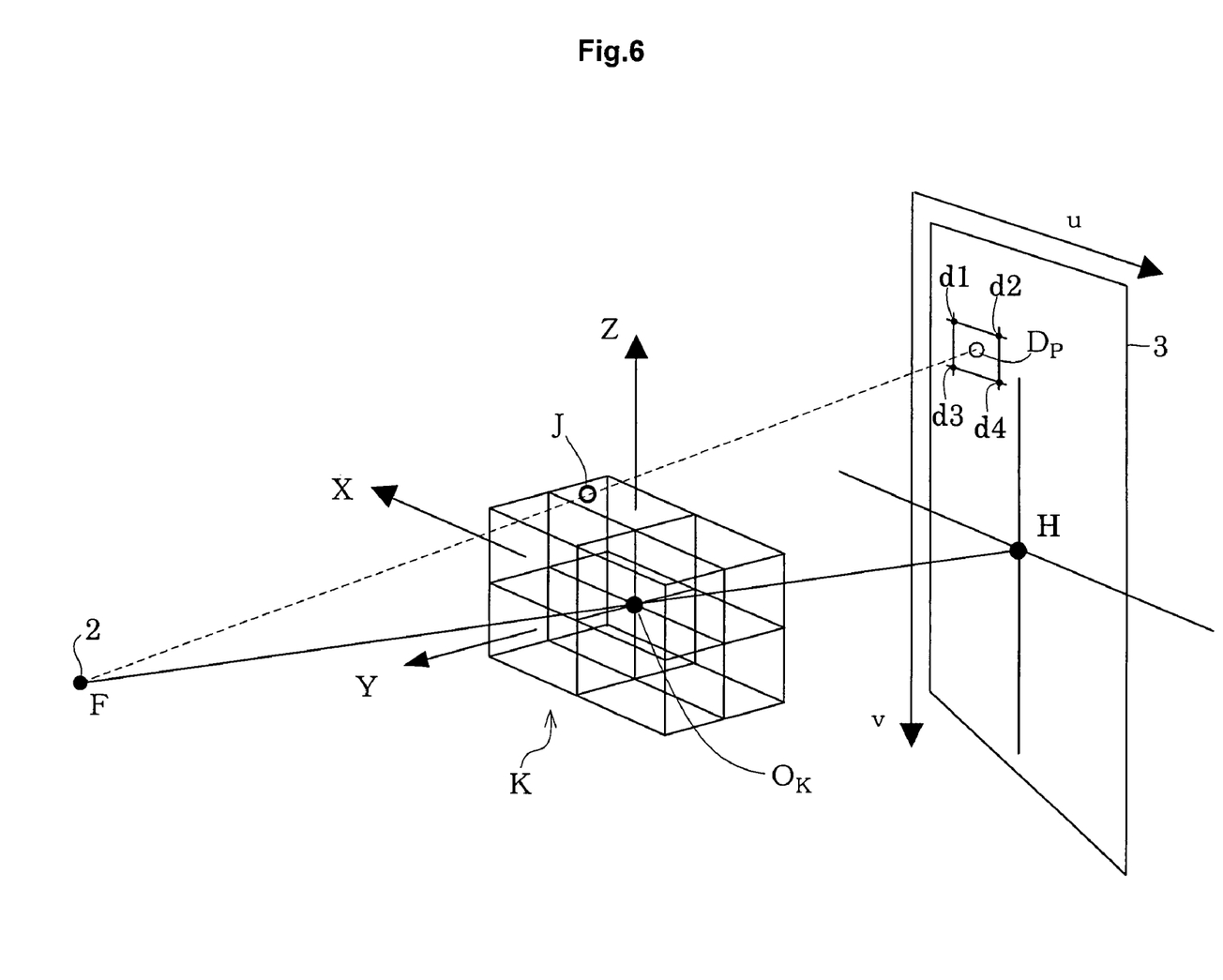
FIG. 6 is a schematic view illustrating a back projection method.

When the simple BP intermediate image is generated, a three-dimensional lattice K is virtually set to the radiographed region of interest of the patient as shown in FIG. 6. Detection data at point $D_P$ on the area detector 3 is back-projected to a lattice point J of the three-dimensional lattice K located on a straight line linking point $D_P$ and X-ray tube 2.

The three-dimensional lattice K is virtually set to the same position as the calibration phantom. That is, the XYZ coordinates of the three-dimensional lattice K are in agreement with the XYZ coordinates of the calibration phantom radiographed by following the same track and the same sequence. Therefore, the coordinates of the lattice point J are accurately derived from the position of the point $D_P$ acquired in radiography of the patient based on the three-dimensional position information on the X-ray tube 2 and area detector 3 relative to the calibration phantom obtained in step S2. The detection data at point $D_P$ is determined, for example, by obtaining a weighted mean of values of four pixels d1–d4 closest to the point $D_P$. Such detection data is obtained from various angles and accumulated on the lattice point, thereby realizing the back projection to the lattice point. A similar back projection is carried out for the remaining lattice points of the three-dimensional lattice K. Further, a similar back projection is carried out for all of the scan positions, thereby to generate a simple BP intermediate image. A blur preventive filtering process and the like may be applied to radiographic images of the patient beforehand.

Then, slice images and/or three-dimensional volume data created of a selected site of the patient are stored in the slice image and three-dimensional volume data storage unit 16, and outputted to the image display 10 as necessary (S7).

After step S7, a further image processing may be carried out on the slice images and/or three-dimensional volume data to be stored and displayed. Such images and/or data may be transferred to other apparatus via a network or media.

Next, the calibration phantom FS for precession tracks and calibration phantom FA for arcuate tracks (circular tracks) used in the above embodiment will be described.

Figure 7:
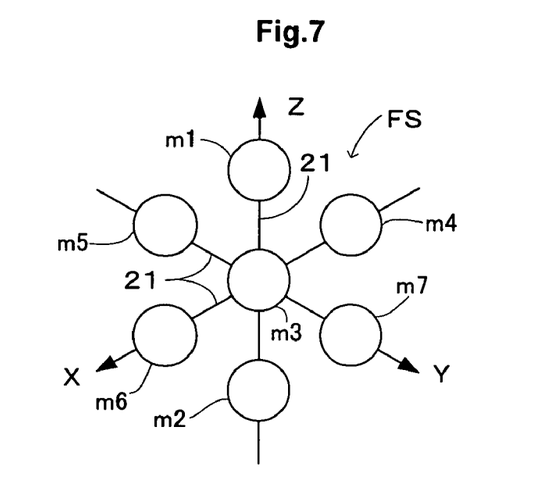
FIG. 7 is a schematic view of a calibration phantom for precession tracks.

(1) Calibration Phantom FS for Precession Tracks:

As schematically shown in FIG. 7, the calibration phantom FS for precession tracks includes a support member 21 formed of a low X-ray absorber and extending in the three-dimensional, XYZ directions, a marker m3 in the form of a steel ball of a high X-ray absorber disposed in a reference position serving as the starting point or origin, and markers m1, m2, m4, m5, m6 and m7 which are steel balls similar to the marker m3 and arranged in positive and negative positions in the three-dimensional, XYZ directions from the marker m3. When this calibration phantom FS for precession tracks is radiographed, no overlapping occurs among projection images of the markers m1, m2, m3, m4, m5, m6 and m7. Thus, the calibration phantom FS provides the advantage of facilitating detection of the positions of the markers m1, m2, m3, m4, m5, m6 and m7.

Figure 8:
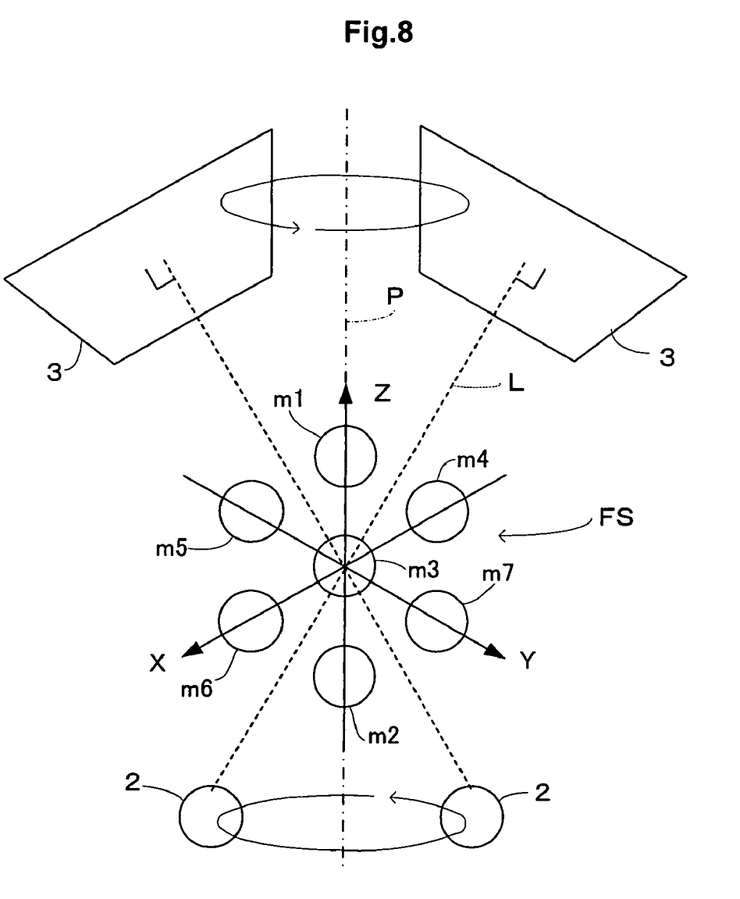
FIG. 8 is a schematic view illustrating the precession tracks.

The precession tracks refer to tracks along which the X-ray tube 2 and area detector 3 rotate, as schematically shown in FIG. 8, about a straight line P (forming, for example, an angle of 15° with a segment L) intersecting the segment L extending between the X-ray tube 2 and a given point on the area detector 3.

This invention is not limited to the above precession tracks. For example, the tracks may be elliptical or more complicated tracks. In half-way positions of the tracks, the straight line may form a different angle with the segment L extending between the X-ray tube 2 and a given point on the area detector 3. The distance from the rotation axis P to X-ray tube 2 or area detector 3 may vary. Backlashes of the mechanism may displace the X-ray tube 2 and area detector 3 on discontinuous tracks for each projection.

Figure 9A:
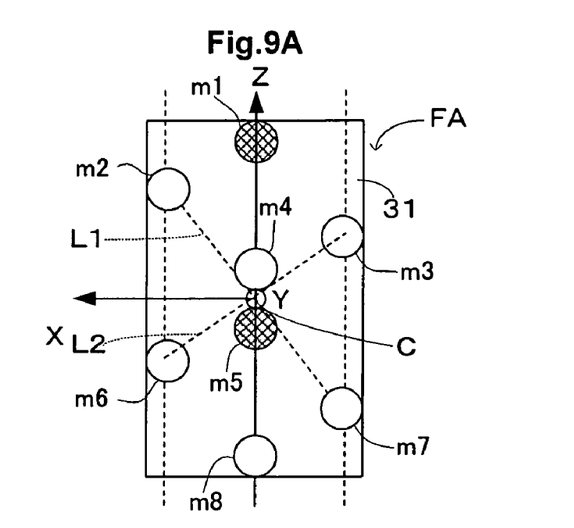
FIG. 9A is a side view of a calibration phantom for arcuate tracks.
Figure 9B:
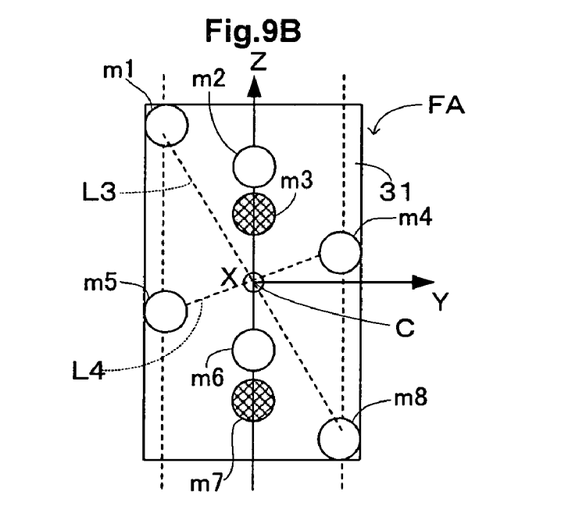
FIG. 9B is a side view rotated 90° of the calibration phantom for arcuate tracks.
Figure 9C:
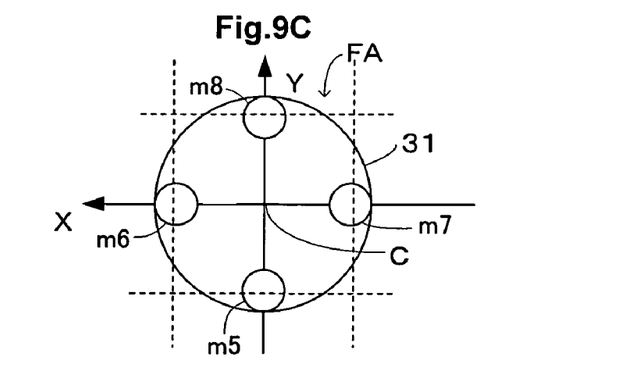
FIG. 9C is a plan view of the calibration phantom for arcuate tracks.

(2) Calibration Phantom FA for Arcuate Tracks (circular tracks):

As shown in FIGS. 9A, 9B and 9C, the calibration phantom FA for arcuate tracks (circular tracks) includes a cylindrical support member 31 formed of a low X-ray absorber, and four sets of, eight markers m1, m2, m3, m4, m5, m6, m7 and m8 in the form of steel balls of a high X-ray absorber arranged in positions of point symmetry about the center of the calibration phantom FA serving as the origin of coordinates.

Figure 10:
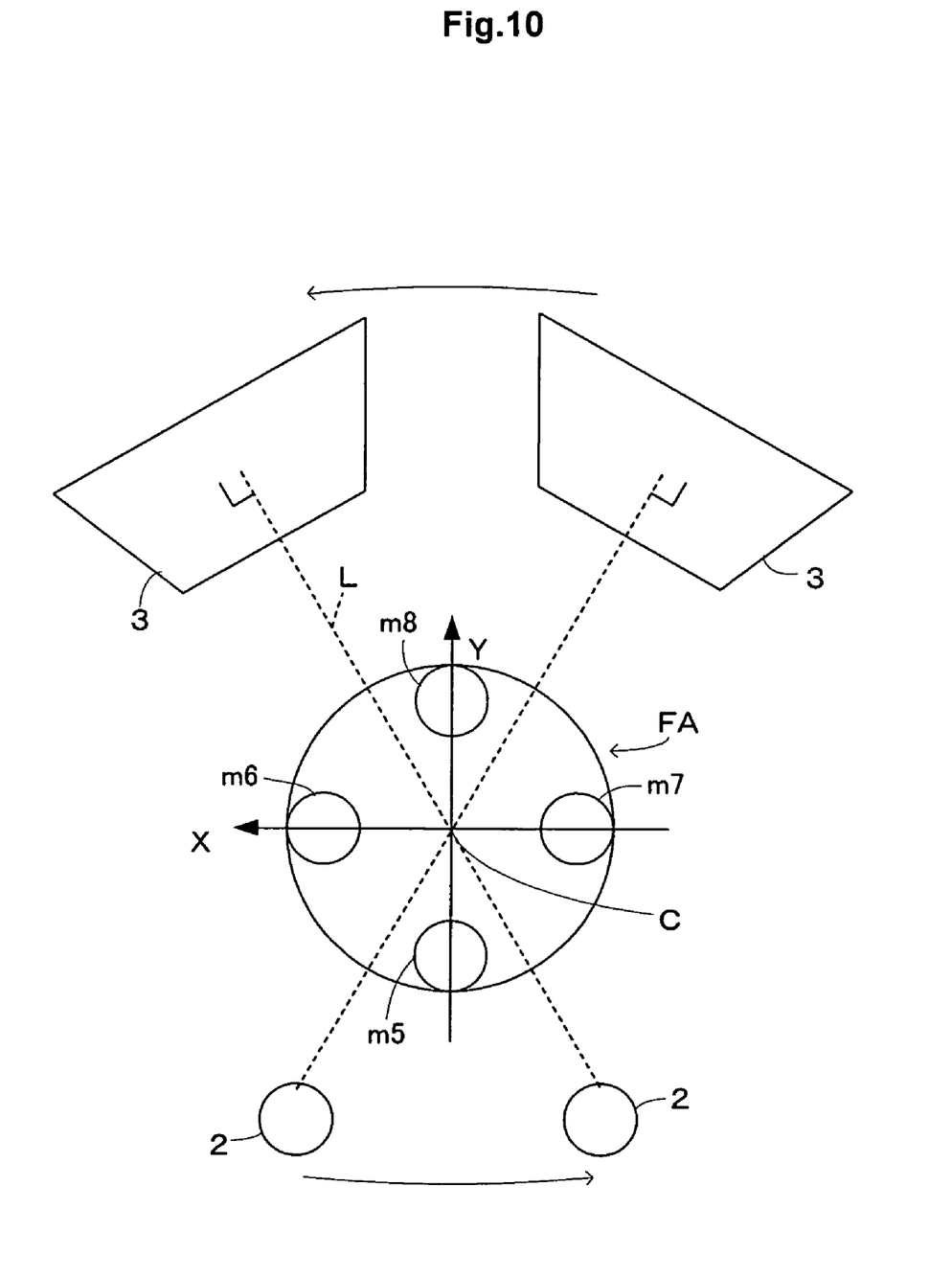
FIG. 10 is a schematic view illustrating the arcuate tracks.

With this construction, as schematically shown in FIG. 10, the X-ray tube 2 and area detector 3 may take radiographic action while rotating about a straight line intersecting a segment L extending between the X-ray tube 2 and a given point on the area detector 3. At this time, as shown in FIG. 9A, an intersection of a segment L1 extending between the markers m2 and m7 and a segment L2 extending between the markers m3 and m6 may be determined. As shown in FIG. 9B, an intersection of a segment L3 extending between the markers m1 and m8 and a segment L4 extending between the markers m4 and m5 may be determined. In this way, coordinates of incident positions on the area detector 3 of X rays having passed through the center C of the calibration phantom FA for arcuate tracks (circular tracks) are calculated. It is therefore unnecessary to provide a marker at the center C of the calibration phantom FA. This provides advantages of allowing the calibration phantom FA for arcuate tracks (circular tracks) simple in construction and inexpensive, and avoiding a reduction in accuracy.

The arcuate tracks (circular tracks) refer to tracks along which the X-ray tube 2 and area detector 3 rotate about a straight line, acting as a rotation axis, intersecting the segment L extending between the X-ray tube 2 and the given point on the area detector 3. The X-ray tube 2 and the given point on the area detector 3 are constantly present in a plane perpendicular to the rotation axis. In FIGS. 9A and 9B, the shaded markers are those located in back positions.

FIG. 10 shows a rotating angle of several tens degrees. However, this invention is not limited to a particular angle, The tracks may describe a full 360° as in a CT apparatus. The distance from the rotation axis to the X-ray tube 2 or area detector 3 may vary, depending on projecting positions. Tracks may displace the X-ray tube 2 and area detector 3 from a fixed plane. Backlashes of the mechanism may displace the X-ray tube 2 and area detector 3 on discontinuous tracks for each projection.

The X-ray tube 2 and area detector 3 may have scanning tracks in the form of two parallel straight lines or similar lines. In short, any tracks are conceivable as long as projection images of the patient are obtained from a plurality of different directions.

Where, for example, the three-dimensional position information includes specified values for mechanical precision that pose no error problem, such as the distance from the origin to the X-ray tube 2 or area detector 3, it is preferable to use such specified values when calculating the three-dimensional position information from the projection images of the calibration phantom. This is because the number of variables required for the reconstructing calculation is reduced to increase processing speed.

In the above embodiment, the X-ray tube 2 that emits X rays is used as the irradiating device. This invention can use devices that emit various electromagnetic waves, such as visible light, X rays from a plasma X-ray source, gamma ray from a radioisotope, X rays from an electronic lilac, or a synchrotron orbital radiation source (SOR).

The above embodiment uses the area detector 3 as the planar detecting device. The invention may use an image intensifier or multi-line detector, instead.

In the above embodiment, the image pickup unit 5 has the X-ray tube 2 and area detector 3 held and mechanically joined by the C-shaped arm 4. However, the invention is not limited to the construction having the C-shaped arm 4 as long as the actuator 6 can move the X-ray tube 2 and area detector 3 as synchronized with each other. The actuator 6 may move the X-ray tube 2 and area detector 3 as synchronized with each other, for example, with a construction in which the X-ray tube 2 and area detector 3 are held individually and connected to a common drive shaft. Further, a construction may be adopted for moving the X-ray tube 2 and area detector 3 as synchronized with each other, in which, while the X-ray tube 2 and area detector 3, the actuator 6 drives the X-ray tube 2 and area detector 3 individually and as synchronized with each other.

This invention may be embodied in other specific forms without departing from the spirit or essential attributes thereof and, accordingly, reference should be made to the appended claims, rather than to the foregoing specification, as indicating the scope of the invention.

What is claimed is:

1. A slice image and/or three-dimensional image creating method for creating images by using a radiographic apparatus that creates slice images and/or three dimensional images from projection images obtained by detecting an electromagnetic wave emitted to an object under examination, said apparatus including:

irradiating means for emitting the electromagnetic wave in a diverging form to the object;

planar detecting means opposed to said irradiating means across the object and having a plurality of pixels in an array arrangement for detecting the electromagnetic wave transmitted through the object;

moving means for moving said irradiating means and said planar detecting means as interlocked to each other; and image creating means for obtaining projection images of the object by emitting the electromagnetic wave from different directions to the object by action of said moving means, and carrying out a reconstruction calculation of the projection images to create slice images and/or three-dimensional images of a selected site of the object;

said method comprising, executed by said image creating means:

a step of obtaining projection images of a calibration phantom serving as the object under examination and having at least three sets of markers, each set including two markers arranged in positions of point symmetry about an origin of coordinates, all said markers being arranged in different planes, and a cylindrical support member for holding said markers;

a step of obtaining three-dimensional position information on said irradiating means and said planar detecting means relative to said calibration phantom based on the projection images of the calibration phantom and three-dimensional arrangement information on said markers inside the calibration phantom; and a step of carrying out the reconstruction calculation of the projection images to create the slice images and/or the three-dimensional images of the selected site of the object, the reconstruction calculation being based on the three-dimensional position information on said irradiating means and said planar detecting means.

2. A method as defined in claim 1, wherein said calibration phantom includes a support member formed of a low X-ray absorber, and spherical markers formed of a high X-ray absorber.

3. A method as defined in claim 2, wherein said markers are steel balls.

4. A method as defined in claim 1, wherein said image creating means includes a three-dimensional position information detecting unit for obtaining the three-dimensional position information on said irradiating means and said planar detecting means relative to said calibration phantom, a three-dimensional position information storage unit for storing the three-dimensional position information obtained, and a reconstruction calculating unit for carrying out the reconstruction calculation of the object based on the three-dimensional position information stored in said three-dimensional position information storage unit, to create slice images and/or three-dimensional images of the selected site of the object.

5. A method as defined in claim 4, wherein said three-dimensional position information detecting unit is arranged to obtain the three-dimensional position information on said irradiating means and said planar detecting means by solving a plurality of equations formed by substituting the three-dimension arrangement information on said markers and two-dimensional position information on the projection images of said markers obtained from the projection images of said calibration phantom, into a relational expression concerning a relationship between positions of the markers, the projection images of the markers, the irradiating means and the planar detecting means.

6. A method as defined in claim 4, wherein said reconstruction calculating unit is arranged to generate the three-dimensional volume data by back-projecting the projection images of the object to a three-dimensional lattice virtually set to a region of interest of the object.

7. A method as defined in claim 1, wherein said image creating means has a slice image and three-dimensional volume data storage unit for storing the slice images and/or three-dimensional images created.

8. A method as defined in claim 1, wherein said moving means is arranged to rotate said irradiating means and said planar detecting means along precession tracks or arcuate tracks.

9. A method as defined in claim 1, wherein said apparatus further comprises image display means for displaying the slice images and/or three-dimensional images created by said image creating means.

10. A method as defined in claim 1, wherein said irradiating means is arranged to emit X rays, and said planar detecting means is arranged to detect the X rays.

11. A method as defined in claim 1, wherein:

said calibration phantom includes markers disposed on each of an origin of XYZ coordinates, positive and negative positions in three directions along an X-axis, a Y-axis and a Z-axis; and said moving means is arranged to rotate said irradiating means and said planar detecting means along precession tracks.

12. A method as defined in claim 1, wherein:

said calibration phantom includes four sets of markers, each set including two markers arranged in the positions of point symmetry about the origin of coordinates; and said moving means is arranged to rotate said irradiating means and said planar detecting means along arcuate tracks.

* * * * *